(12) United States Patent
Hase

(10) Patent No.: US 9,440,004 B2
(45) Date of Patent: Sep. 13, 2016

(54) METHOD FOR PREPARING BIOLOGICAL TISSUE

(75) Inventor: Masahiko Hase, Tokyo (JP)

(73) Assignee: DAI NIPPON PRINTING CO., LTD., Tokyo (JP)

(*) Notice: Subject to any disclaimer, the term of this patent is extended or adjusted under 35 U.S.C. 154(b) by 594 days.

(21) Appl. No.: 12/686,360

(22) Filed: Jan. 12, 2010

(65) Prior Publication Data
US 2010/0190246 A1   Jul. 29, 2010

(30) Foreign Application Priority Data
Jan. 13, 2009   (JP) ................................ 2009-005190

(51) Int. Cl.
| A61L 27/38 | (2006.01) |
| C12N 5/00  | (2006.01) |
| A61K 35/12 | (2015.01) |

(52) U.S. Cl.
CPC ......... *A61L 27/3895* (2013.01); *C12N 5/0062* (2013.01); *A61K 35/12* (2013.01); *C12N 2525/00* (2013.01); *C12N 2535/10* (2013.01)

(58) Field of Classification Search
CPC .............. C12N 13/00; C12N 2506/00; C12N 2527/00; C12N 2529/00; C12N 2537/00; C12N 2539/00; C12N 5/0062; C12N 2535/10; C12N 2525/00; C12M 35/02; C12M 35/04; C12M 35/06; A61L 27/3895; A61K 35/12
USPC ................. 435/173.1, 325, 395, 29
See application file for complete search history.

(56) References Cited

U.S. PATENT DOCUMENTS

| 2003/0224510 A1* | 12/2003 | Yamaguchi et al. .......... 435/366 |
| 2004/0028657 A1  | 2/2004  | Okano et al. |
| 2006/0008904 A1  | 1/2006  | Tanaka et al. |
| 2006/0063252 A1  | 3/2006  | Ito et al. |
| 2006/0121606 A1  | 6/2006  | Ito et al. |
| 2006/0171930 A1  | 8/2006  | Seyda et al. |
| 2007/0148762 A1* | 6/2007  | Miyake et al. ............ 435/289.1 |
| 2009/0075363 A1  | 3/2009  | Morimoto et al. |
| 2010/0184182 A1  | 7/2010  | Hase |
| 2010/0184222 A1  | 7/2010  | Hase |
| 2010/0190253 A1  | 7/2010  | Tazaki et al. |
| 2011/0151565 A1  | 6/2011  | Hase et al. |

FOREIGN PATENT DOCUMENTS

| JP | 2003070466    | 3/2003  |          |
| JP | 2004-81090 A  | 3/2004  |          |
| JP | 2004254519    | 9/2004  |          |
| JP | 2005312386    | 11/2005 |          |
| JP | 2006204168    | 8/2006  |          |
| JP | 2007229249    | 9/2007  |          |
| JP | 3139350       | 2/2008  |          |
| JP | 4084386 B2    | 4/2008  |          |
| JP | 2008132126    | 6/2008  |          |
| JP | 2008523957    | 7/2008  |          |
| JP | 2010161952    | 7/2010  |          |
| JP | 2010161954    | 7/2010  |          |
| WO | 0210349       | 2/2002  |          |
| WO | 2004/083412 A1| 9/2004  |          |
| WO | 2004083416    | 9/2004  |          |
| WO | 2004101774    | 11/2004 |          |
| WO | WO2006136953 A2 * | 12/2006 | .............. C12N 5/06 |
| WO | WO 2007087402 A2 * | 8/2007 | .............. C12M 3/00 |
| WO | 2007116594    | 10/2007 |          |
| WO | 2007126127    | 11/2007 |          |
| WO | WO2008066965 A2 * | 6/2008 | .............. A61K 35/12 |
| WO | 2008143149    | 11/2008 |          |
| WO | 2008156041    | 12/2008 |          |

OTHER PUBLICATIONS

Wang et al. Generation of Three-Dimensional Hepatocyte/Gelatin Structures with Rapid Prototyping System. Tissue Engineering. vol. 12, No. 1, 2006. p. 83-90.*
Dessau et al. Synthesis and Extracellular Deposition of Fibronectin in Chondrocyte Cultures. J. Cell Biology. vol. 79 Nov. 1978 p. 342-355.*
Cramton et al. The Intercellular Adhesion (ica) Locus is Present in *Staphylococcus aureus* and is Required for Biofilm Formation. Infection and Immunity,Oct. 1999, p. 5427-5433.*
Jarvis et al. Intercellular adhesion and cell separation in plants. Plant, Cell and Environment (2003) 26, 977-989.*
Ito et al. Novel Methodology for Fabrication of Tissue-Engineered Tubular Constructs Using Magnetite Nanoparticles and Magnetic Force. Tissue Engineering vol. 11, No. 9/10, 2005. p. 1553-1561.*
Akira Ito, et al; "Construction and Harvest of Multilayered Keratinocyte Sheets Using Magnetite Nanoparticles and Magnetic Force"; Tissue Engineering; 2004; pp. 873-881; vol. 10, No. 5/6.
Office Action for Japanese Patent Application No. 2009-005190 dated Jun. 25, 2013.

\* cited by examiner

*Primary Examiner* — Taeyoon Kim
(74) *Attorney, Agent, or Firm* — Sughrue Mion, PLLC

(57) ABSTRACT

This invention provides a method for obtaining biological tissue having a three-dimensional structure of interest. The method of the invention comprises: adding a cell-containing culture solution to a culture vessel having an inner bottom surface, which is non-cell adhesive and comprises a concave-convex pattern provided thereon; performing cell culture under conditions in which intercellular adhesion takes place while centrifugal or magnetic force toward the inner bottom surface is applied to the cells that were added to the culture vessel to form tissue via intercellular adhesion; and detaching and collecting the resulting tissue from the inner bottom surface at the end in order to obtain tissue having a three-dimensional configuration using a concave-convex pattern as a template.

8 Claims, 14 Drawing Sheets

(7 of 14 Drawing Sheet(s) Filed in Color)

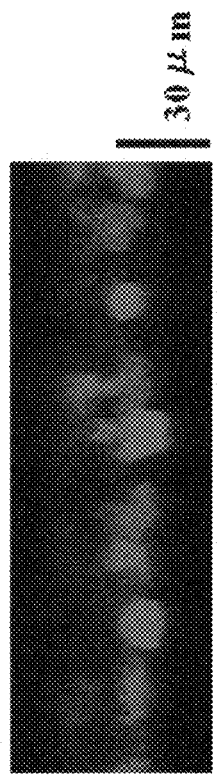
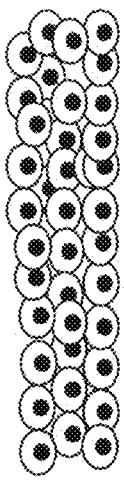
Fig. 9

METHOD FOR PREPARING BIOLOGICAL TISSUE

TECHNICAL FIELD

The present invention relates to a method for preparing biological tissue that is suitable for preparation of biological tissue having a multilayer structure of a plurality of superposed cells in the through-thickness direction.

BACKGROUND ART

Biological tissue that is prepared via cell culture on a culture support such as collagen has low cell density. Accordingly, such biological tissue is not suitable as transplant tissue for medical purposes. A technique for preparing tissue suitable for transplantation, such as a cell sheet with high cell density, can be said to be an important technique in the tissue engineering field. However, existing methods for preparing biological tissue with high cell density have several drawbacks.

In general, sowing of cells on a culture support to form a cell sheet is extensively carried out. In order to facilitate detachment of a cell sheet, a technique of providing a layer of a temperature-responsive polymer compound on a cell adhesion surface to accelerate cell detachment has been developed. A cell sheet formed via such technique, however, is generally composed of a single layer or three or fewer cell layers. Accordingly, it is necessary to superpose a plurality of cell sheets in order to form a multilayer structure. Since a cell sheet is very thin and difficult to handle, superposition of a plurality of such cell sheets is laborious rather than easy.

Patent Document 1 and Non-Patent Document 1 each disclose a method for easily preparing a multilayered cell sheet in which cells are allowed to support magnetic fine particles thereon, magnetized cells are sowed in a culture vessel having a non-cell-adhesive bottom surface, the magnetized cells are affixed to the bottom surface with magnetic force, cell culture is conducted to form tissue, and tissue is collected via removal of the magnetic force at the end. This technique enables preparation of multilayered cells without the need for superposition of cell sheets. According to the method disclosed in Cited Document 1, however, multiple cell layers are flatly superposed on top of each other. Thus, nutrition supply to cells that are present inside the tissue and discharge of wastes from such cells were insufficient, and cellular necrosis was likely to take place.

Meanwhile, a method in which cells are exposed to centrifugal force during cell culture had been employed in the past for the purpose of imposing stimuli to cultured cells. For example, Patent Document 2 discloses a method for stimulating cells by regulating the dynamic environment with the application of hydrostatic pressure by centrifugal force under cell culture conditions for the purpose of suppressing cell dedifferentiation. Patent Document 2, however, does not refer to any method for detaching formed tissue. Also, what is disclosed in Patent Document 2 is a method in which centrifugal force is intermittently applied while growing cells over the period of several weeks. With such method, a tissue mass of weakly adhering spherical cells, which are referred to as spheroids, is formed (Patent Document 2, FIG. 6), and, thus, tissue that can be used as a graft, such as a cell sheet, cannot be prepared.

Patent Document 3 discloses a method for preparing a three-dimensional construct from bone cells or the like. According to the method of Patent Document 3, a cell suspension is allowed to stand in a given cloning ring, it is allowed to precipitate once, the cell suspension is allowed to stand further, tissue is formed from the precipitated cells, the tissue-forming cells are subjected to rotation culture so as to enhance oxygen- and nutrition-diffusing effects, and a three-dimensional construct of bone cells or the like with a centimeter-order size is then prepared. However, such technique has drawbacks such that, for example, it takes several days to prepare tissue, target cells are limited to bone cells or the like, tissue cannot be easily detached from a culture vessel, and a conformation cannot be regulated as intended.

PRIOR ART DOCUMENTS

Patent Documents

Patent Document 1: WO 2004/083412
Patent Document 2: JP Patent Publication (kokai) No. 2004-81090 A
Patent Document 3: JP Patent No. 408-4386

Non-Patent Document

Non-Patent Document 1: AKIRA ITO, et al., Tissue Engineering, Volume 10, Number 5/6, 873-880, 2004

SUMMARY OF THE INVENTION

Problem to be Solved by the Invention

Tissue having multiple cell layers could undergo cellular necrosis. Also, there was no method in the past that could provide biological tissue having high cell density and a three-dimensional structure of interest.

It is an object of the present invention to provide a method that can provide biological tissue having a three-dimensional structure of interest; that is, for example, to provide biological tissue comprising a fluid channel for the purpose of preventing cellular necrosis.

Means for Solving the Problem

Surprisingly, the present inventors found that such problem can be solved by adding a cell-containing culture solution to a culture vessel having an inner bottom surface, which is or can be converted into a non-cell-adhesive surface and comprises a concave-convex pattern provided thereon, and conducting culture by applying centrifugal or magnetic force toward the inner bottom surface to the cells. This has led to the completion of the present invention. The present invention includes the following.

(1) A method for preparing tissue comprising:
a step of cell addition comprising adding a cell-containing culture solution to a culture vessel having an inner bottom surface, which is or can be converted into a non-cell-adhesive surface and comprises a concave-convex pattern provided thereon;
a step of cell culture comprising performing cell culture under conditions in which intercellular adhesion takes place while centrifugal or magnetic force toward the inner bottom surface is applied to the cells that were added to the culture vessel to form tissue via intercellular adhesion; and
a step of detachment comprising detaching and collecting the tissue obtained in the step of cell culture from the inner bottom surface,
the method further comprising, when magnetic force is applied in the step of cell culture, a step of magnetization comprising magnetizing cells with magnetic fine particles prior to the step of cell addition.

(2) The method according to (1), wherein the number of cells in the culture solution is regulated in accordance with the number of cell layers in the through-thickness direction of tissue to be prepared.

(3) The method according to (1) or (2), wherein the culture solution contains an extracellular matrix component in a dissolved or dispersed state.

(4) The method according to (3), wherein the extracellular matrix component is prepared from cells derived from an individual identical to that from which the cells to be cultured are derived.

(5) The method according to any of (1) to (4), wherein a configuration of the concave-convex pattern enables detachment of tissue formed on the inner bottom surface of the culture vessel while maintaining the tissue configuration.

(6) The method according to any of (1) to (5), wherein the concave-convex pattern comprises a plurality of island-like convex portions and sea-like concave portions continuously formed around the convex portions and the number of cells in a culture solution is regulated, so that the thickness of tissue to be prepared does not exceed the height of the convex portion.

(7) The method according to any of (1) to (6), wherein the step of cell culture comprises performing cell culture under conditions in which intercellular adhesion takes place while centrifugal force toward the inner bottom surface is applied to the cells that were added to the culture vessel to form tissue via intercellular adhesion.

(8) The method according to any of (1) to (7), wherein all portions on the inner surface of the culture vessel that are in touch with cells are or can be made non-cell-adhesive.

(9) Tissue prepared by the method according to any of (1) to (8).

(10) The tissue according to (9), wherein a plurality of cells are superposed in the through-thickness direction.

(11) The tissue according to (10), which comprises through-holes in the through-thickness direction.

Effects of the Invention

According to the method for preparing tissue of the present invention, biological tissue having a three-dimensional structure of interest can be easily obtained.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9 shows that the cell sheet prepared in Reference Example 1 has a multilayer structure.

EMBODIMENTS FOR CARRYING OUT THE INVENTION

Figure 1:
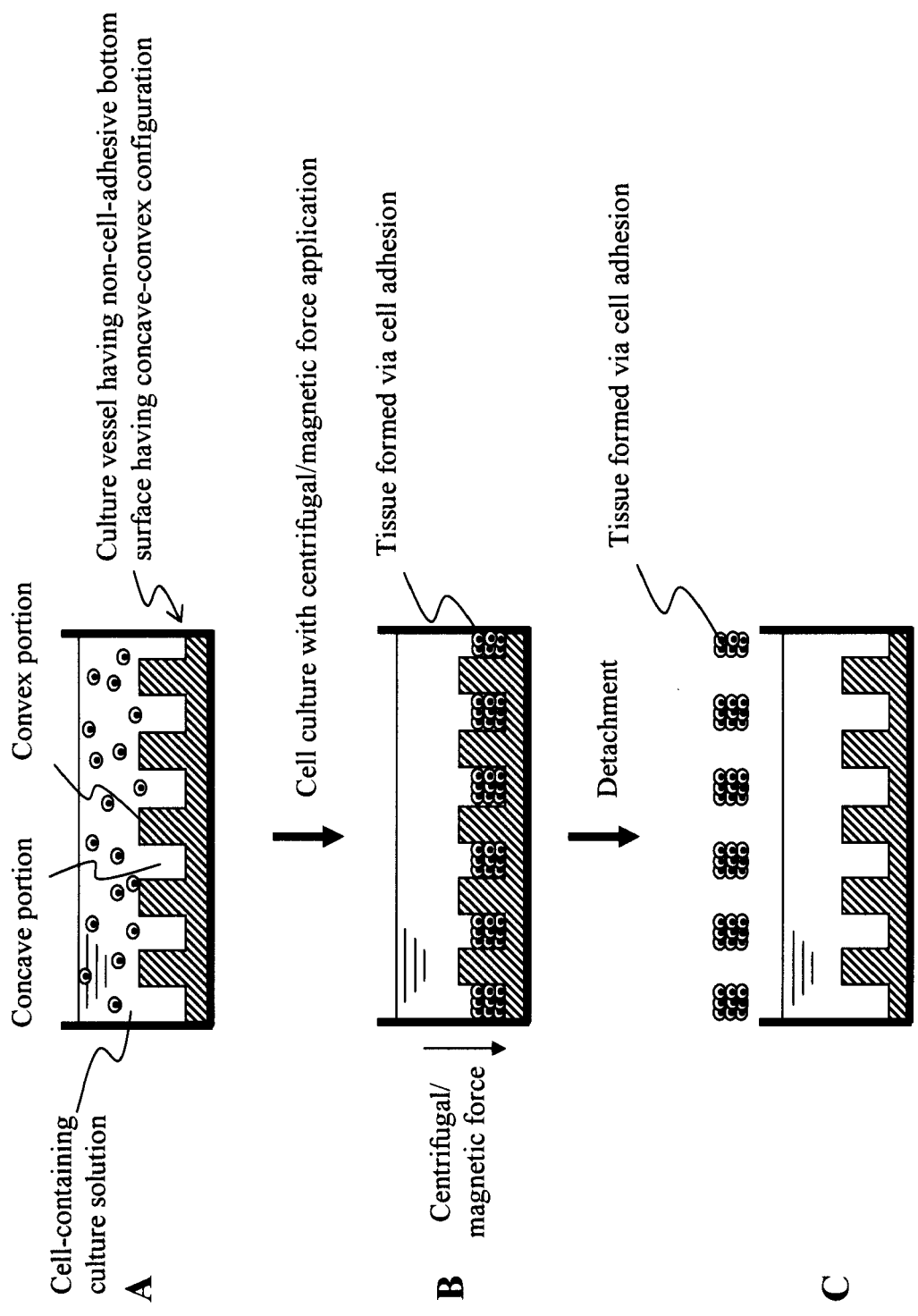
FIG. 1 shows a procedure for preparing biological tissue according to the present invention.

According to the present invention, a cell-containing culture solution is first added to a culture vessel having inner surfaces, with at least the inner bottom surface being non-cell-adhesive or capable of being made non-cell-adhesive and a concave-convex pattern provided thereon, as shown in FIG. 1A. Subsequently, centrifugal or magnetic force toward the inner bottom surface is applied to cells that had been added to the culture vessel, and cell culture is performed under conditions in which intercellular adhesion takes place to form tissue via intercellular adhesion, as shown in FIG. 1B. In this case, cells migrate toward the bottom surface and accumulate with the aid of centrifugal or magnetic force, and cells adhere to each other to form tissue. Finally, the formed tissue is detached and collected from the inner bottom surface to obtain tissue having a three-dimensional structure using a concave-convex pattern as a template. Hereafter, the features of the present invention are described.

1. Culture Vessel

A culture vessel used in the present invention may have inner surfaces of a vessel that accommodates a cell-containing culture solution, with at least the inner bottom surface being non-cell-adhesive or capable of being made non-cell-adhesive. Particularly preferably, all surfaces that are in contact with cells of the inner surfaces of a vessel that accommodates a cell-containing culture solution (e.g., the inner bottom surface and the inner side surface of the vessel) are or can be made non-cell-adhesive.

A concave-convex pattern on the inner bottom surface of the culture vessel can be adequately selected, so that tissue has a three-dimensional structure of interest.

Figure 14:
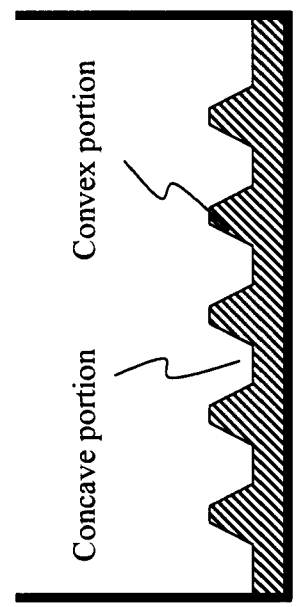
FIG. 14 shows an embodiment of a concave portion with an inclined side wall surface.

Preferably, a concave-convex pattern enables detachment of tissue formed on the inner bottom surface of the culture vessel (such tissue is prepared using a concave-convex pattern as a template and thus has at least in part an inverted pattern of the concave-convex pattern) while maintaining the tissue configuration. Typical examples of such configurations include a concave-convex pattern in which the side walls of the concave portion on the cross-section of the concave portion along with a plane vertical to the bottom surface of the culture vessel are provided parallel to the axis passing through the space inside the concave portion and being vertical to the bottom surface of the culture vessel (e.g., the configuration shown in FIG. 1), a concave-convex pattern in which a distance between such axis and the side wall of the concave portion becomes larger from a closed end of the concave portion toward an open end thereof (e.g., the configuration shown in FIG. 14), and a concave-convex pattern comprising both such configurations. Such configuration of the concave portion is preferable since such configuration enables detachment of the formed tissue from the concave-convex pattern without destruction of the inverted pattern of tissue.

Figure 2:
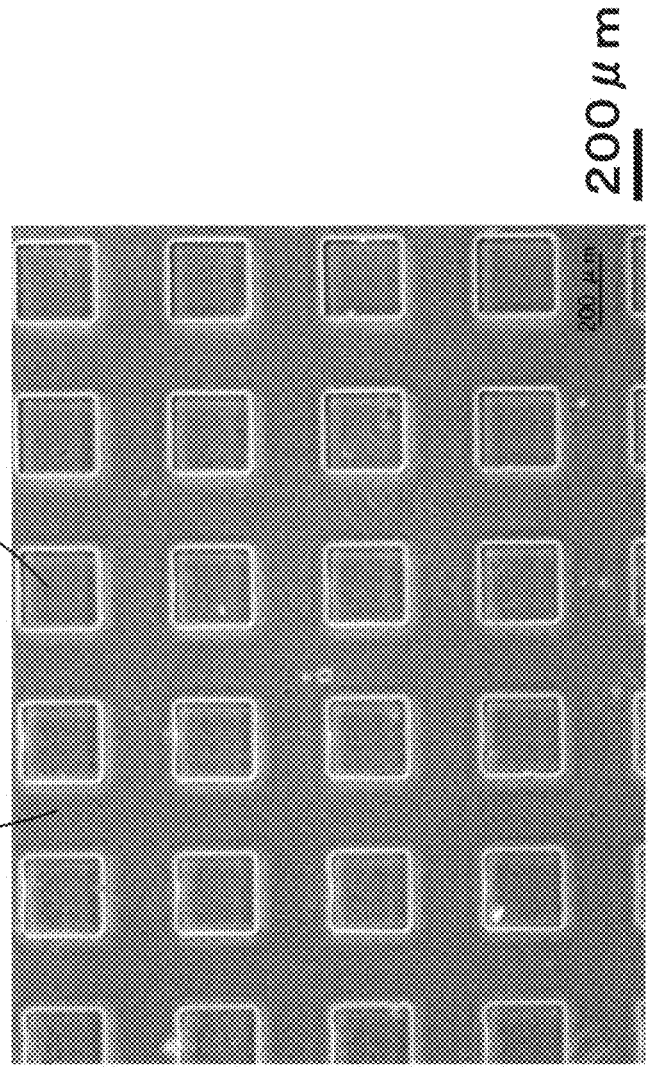
FIG. 2 shows a non-cell-adhesive bottom surface of a culture vessel comprising a concave-convex pattern composed of island-like convex portions and sea-like concave portions.
Figure 3:
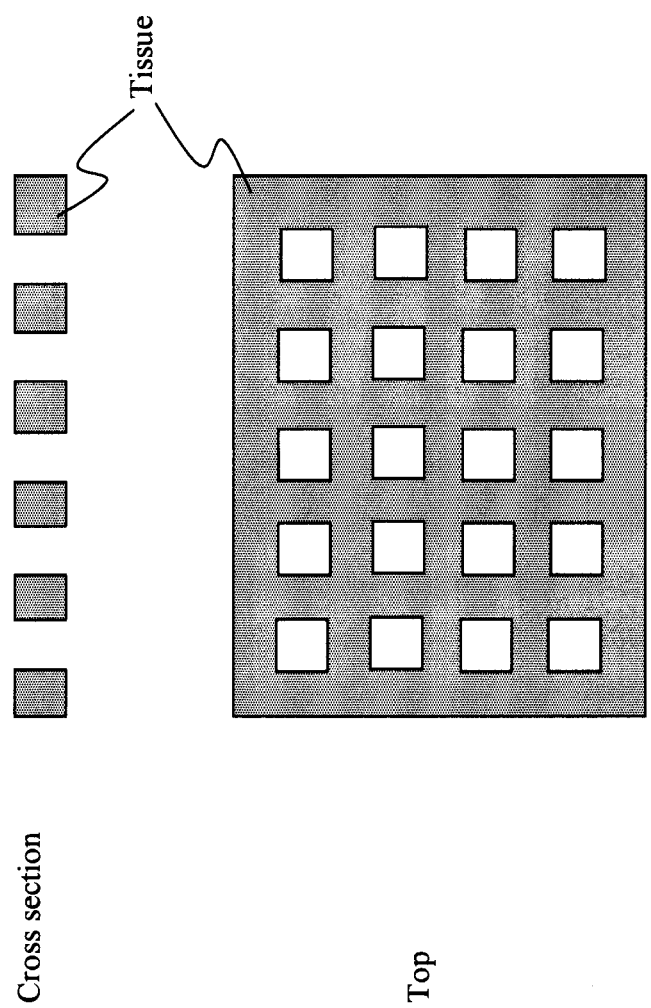
FIG. 3 schematically shows biological tissue prepared with the use of the culture vessel having a concave-convex pattern on the bottom surface shown in FIG. 2.

A particularly preferable concave-convex pattern comprises a plurality of island-like convex portions and sea-like concave portions continuously formed around such convex portions. An example of such concave-convex pattern is shown in FIG. 2. With the use of the culture vessel shown in FIG. 2 having the concave-convex pattern at the bottom, cells are accumulated in the concave portion due to centrifugal or magnetic force, and such cells adhere to each other. When the number of cells in the culture solution is regulated so as to prevent the thickness of the prepared tissue from exceeding the height of the convex portion, lattice-like tissue having through-holes in the through-thickness direction is formed as shown in FIG. 3. Such through-holes function as routes of nutrition supply to the inside of tissue and as routes of waste discharge. If cell sheets without through-holes are merely superposed, cellular necrosis takes places. If through-holes are formed according to the present embodiment, however, cellular necrosis can be suppressed. While through-holes could be formed on a monolayer cell sheet according to conventional techniques, through-holes had to be aligned with each other in order to form a multilayer structure. Since through-holes are very fine, there is no practical means for realizing alignment thereof at present. The present embodiment is very useful since formation of multilayered cells and formation of a fluid passage can be simultaneously carried out.

Figure 13:
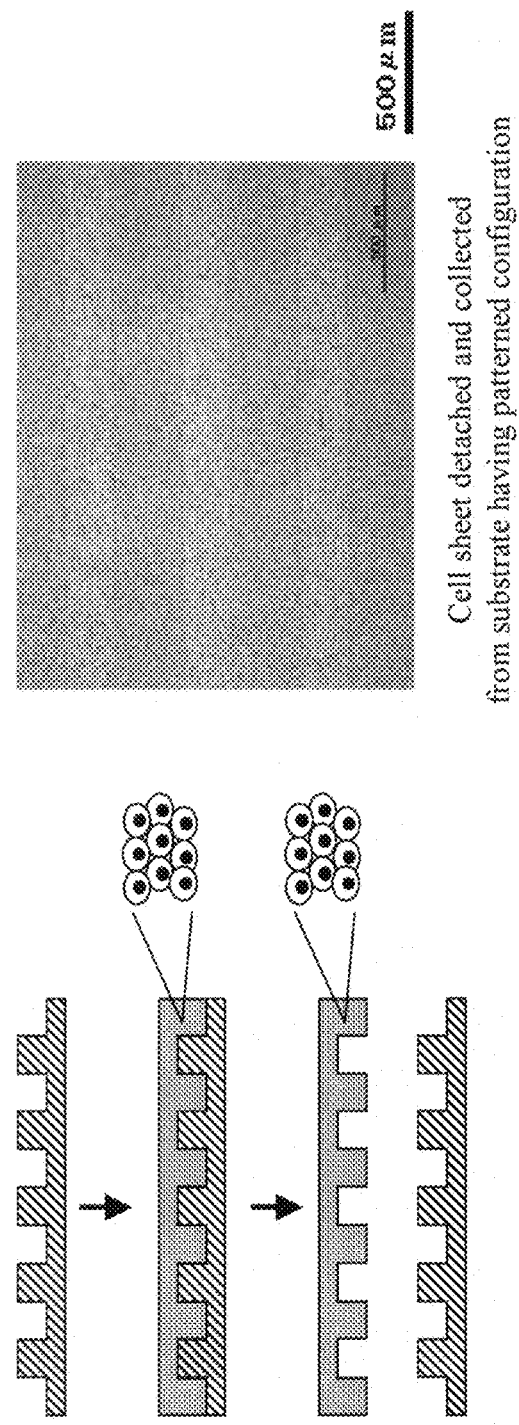
FIG. 13 shows a cell sheet prepared in Example 2 having a concave-convex pattern on the surface.

As shown in FIG. 13 (Example 2), the number of cells in the culture solution may be regulated so as to cover the top surfaces of concave portions as well as convex portions on the inner bottom surface of the culture vessel with cells, upon application of centrifugal or magnetic force. Thus, an inverted pattern of the concave-convex pattern on the inner bottom surface of the culture vessel can be formed on the tissue surface.

Another embodiment of a concave-convex pattern is a concave-convex pattern comprising convex ribs and concave grooves that are alternately arranged in parallel.

A method for forming a concave-convex pattern is not particularly limited, and a concave-convex pattern can be formed via general fine processing technologies.

In the present invention, an example of a non-cell-adhesive surface is a hydrophilic surface, and a specific example is a surface having a static water contact angle of 45 degrees or less at 20° C. Such surface can be obtained by forming a coating of an organic compound having a carbon-oxygen bond on the substrate surface. Alternatively, a substrate may be composed of a hydrophilic material.

A substrate material used for forming a hydrophilic coating on the surface is not particularly limited. Specific examples include inorganic materials, such as metals, glass, ceramics, and silicon, and organic materials represented by elastomers and plastics (e.g., polyester resin, polyethylene resin, polypropylene resin, ABS resin, nylon, acrylic resin, fluorine resin, polycarbonate resin, polyurethane resin, methylpentene resin, phenol resin, melamine resin, epoxy resin, and vinyl chloride resin).

A non-cell-adhesive surface can be formed by a hydrophilic membrane composed of an organic compound having a carbon-oxygen bond and having a static water contact angle of 45 degrees or less.

The term "carbon-oxygen bond" refers to a bond formed between carbon and oxygen. Such bond may be a single or double bond. Examples of carbon-oxygen bonds include C—O bonds, C(=O)—O bonds, and C=O bonds.

Examples of the main raw materials for hydrophilic membranes include hydrophilic organic compounds, such as water-soluble polymers, water-soluble oligomers, water-soluble organic compounds, surface active materials, and amphiphilic materials. When such materials are physically or chemically crosslinked to each other or such materials are physically or chemically bound to substrates, hydrophilic membranes are formed.

Specific examples of water-soluble polymer materials include polyalkylene glycol and a derivative thereof, polyacrylic acid and a derivative thereof, polymethacrylic acid and a derivative thereof, polyacrylamide and a derivative thereof, polyvinyl alcohol and a derivative thereof, a zwitterionic polymer, and a polysaccharide. Examples of molecular shapes include linear polymers, branched polymers, and dendrimers. Specific examples thereof include, but are not limited to, polyethylene glycol, a copolymer of polyethylene glycol and polypropylene glycol (e.g., Pluronic F108, Pluronic F127), poly(N-isopropylacrylamide), poly(N-vinyl-2-pyrrolidone), poly(2-hydroxyethyl methacrylate), poly(methacryloyloxyethyl phosphorylcholine), a copolymer of methacryloyloxyethyl phosphorylcholine and an acrylic monomer, dextran, and heparin.

Specific examples of water-soluble oligomer materials and water-soluble low-molecular compounds include an alkylene glycol oligomer and a derivative thereof, an acrylic acid oligomer and a derivative thereof, a methacrylic acid oligomer and a derivative thereof, an acrylamide oligomer and a derivative thereof, a saponified product of a vinyl acetate oligomer and a derivative thereof, an oligomer comprising zwitterionic monomers and a derivative thereof, an acrylic acid and a derivative thereof, a methacrylic acid and a derivative thereof, acrylamide and a derivative thereof, a zwitterionic compound, a water-soluble silane coupling agent, and a water-soluble thiol compound. More specific examples include, but are not limited to, an ethylene glycol oligomer, an (N-isopropyl acrylamide) oligomer, a methacryloyloxyethyl phosphorylcholine oligomer, low-molecular weight dextran, low-molecular weight heparin, oligoethylene glycol thiol, ethylene glycol, diethylene glycol, triethylene glycol, tetraethylene glycol, 2-[methoxy(polyethyleneoxy)-propyl]trimethoxysilane, and triethylene glycol-terminated-thiol.

The average thickness of a hydrophilic membrane is preferably 0.8 nm to 500 μm, more preferably 0.8 nm to 100 μm, further preferably 1 nm to 10 μm, and most preferably 1.5 nm to 1 μm. The average thickness of 0.8 nm or greater is preferable since the influence imposed by a region that is not coated with the hydrophilic membrane on the substrate surface is insignificant. When the average thickness is 500 μm or smaller, coating is relatively easy.

Examples of methods for forming a hydrophilic membrane on a substrate surface include a method in which a hydrophilic organic compound is directly adsorbed to a substrate, a method in which a substrate is directly coated with a hydrophilic organic compound, a method in which a substrate is coated with a hydrophilic organic compound followed by crosslinking, a method in which a hydrophilic membrane is formed in multiple steps so as to improve adhesion to a substrate, a method in which an underlying layer is formed on a substrate and the resultant is then coated with a hydrophilic organic compound so as to improve adhesion to a substrate, and a method in which a polymerization origin is formed on a substrate surface and a hydrophilic polymer brush is then polymerized.

Among such methods for forming membranes, particularly preferable examples thereof include the method in which a hydrophilic membrane is formed in multiple steps and the method in which an underlying layer is formed on a substrate and the resultant is then coated with a hydrophilic organic compound so as to improve adhesion to a substrate. This is because adhesion of a hydrophilic organic compound to a substrate can be easily improved via such techniques. In this description, the term "bond layer" is used. The term "bond layer" refers to a layer that exists between the outermost hydrophilic membrane and a substrate, when a coating of a hydrophilic organic compound is provided in multiple steps. When a hydrophilic membrane is provided on an underlying layer provided on the substrate surface, the term refers to such underlying layer. A bond layer preferably contains a material having a binding portion (i.e., a linker). Examples of combinations of a linker and a terminal functional group of a material to be bound to a linker include an epoxy group and a hydroxyl group, phthalic anhydride and a hydroxyl group, a carboxyl group and N-hydroxysuccinimide, a carboxyl group and carbodiimide, and an amino group and glutaraldehyde. Either one in such combination may be a linker. In the above-described methods, a bond layer is formed on the substrate with the use of a material containing a linker prior to coating of the substrate with a hydrophilic material. The density of such material in the bond layer is an important factor that defines binding strength. Such density can be easily evaluated by using a water contact angle on the bond layer surface as an indicator. In the case of a silane coupling agent having an epoxy group at the terminus (i.e., epoxysilane), for example, when the substrate surface to which epoxysilane has been applied has a water contact angle of typically 45 degrees or greater, and preferably 47 degrees or greater, an ethylene glycol-based material or the like may be added in the presence of an acid catalyst, so that a surface with sufficient non-cell-adhesive properties can be obtained.

Regions on the inner surfaces that are in contact with cells, including the inner bottom surface of the culture vessel used in the present invention, are preferably non-cell-adhesive, from the viewpoint of ease of detachment of tissue. A surface that is cell adhesive at the time of cell culture but can be made non-cell-adhesive at the time of detachment may also be used. Such surface can be formed via immobilization of a covalent bond on a substrate surface by at least 1 type of stimuli-responsive polymer selected from the group consisting of a temperature-responsive polymer, a pH-responsive polymer, and an ion-responsive polymer. As a stimuli-responsive polymer, a temperature-responsive polymer is particularly preferable, although the polymer is not limited thereto.

A temperature-responsive polymer that can be preferably used in the present invention exhibits hydrophobic properties at a temperature at which cells are cultured (about 37° C. in general) and exhibits hydrophilic properties at a temperature at which the cultured cell sheet is collected. A temperature at which a temperature-responsive polymer is converted from hydrophobic into hydrophilic (i.e., a critical solution temperature T in water) is not particularly limited. From the viewpoint of ease of collection of a cell sheet after culture, such temperature is preferably lower than a temperature at which cells are cultured. By containing such temperature-responsive polymer component, cellular scaffolds (i.e., cell-adhesion surfaces) are sufficiently retained at the time of cell culture. Thus, cell culture can be efficiently carried out. In contrast, a hydrophobic portion may be converted into a hydrophilic portion, and the cultured cell sheet is separated from a cell culture substrate at the time of collection of a cell sheet after culture, so that a cell sheet can be more easily collected. A temperature-responsive polymer exhibiting hydrophilic properties at a temperature lower than a given critical solution temperature and exhibiting hydrophobic properties at a temperature higher than the critical solution temperature is particularly preferable. The critical solution temperature of such temperature-responsive polymer is specifically referred to as a lower limit critical solution temperature.

Specifically, a temperature-responsive polymer that can be preferably used in the present invention has a lower limit critical solution temperature, T, of 0° C. to 80° C., and preferably 0° C. to 50° C. T that is higher than 80° C. is not preferable since cells may be killed. Also, T that is lower than 0° C. is not preferable since, in general, the cell growth rate is lowered to an extreme extent or cells may be killed. Examples of such preferable polymers include acrylic and methacrylic polymers. Specific examples of preferable polymers include poly-N-isopropylacrylamide (T of 32° C.), poly-N-n-propylacrylamide (T of 21° C.), poly-N-n-propyl methacrylamide (T of 32° C.), poly-N-ethoxyethylacrylamide (T of about 35° C.), poly-N-tetrahydrofurfuryl acrylamide (T of about 28° C.), poly-N-tetrahydrofurfuryl methacrylamide (T of about 35° C.), and poly-N,N-diethylacrylamide (T of 32° C.). Examples of other polymers include poly-N-ethylacrylamide; poly-N-isopropyl methacrylamide; poly-N-cyclopropylacrylamide; poly-N-cyclopropyl methacrylamide; poly-N-acryloyl pyrrolidine; poly-N-acryloyl piperidine; polymethyl vinyl ether; alkyl-substituted cellulose derivatives, such as methyl cellulose, ethyl cellulose, and hydroxypropyl cellulose; polyalkylene oxide block copolymers represented by a block copolymer of polypolypropylene oxide and polyethylene oxide; and polyalkylene oxide block copolymers.

Examples of monomers used for forming such polymers include a monomer which can provide, when homopolymerized, T of 0° C. to 80° C. and can be polymerized via radiation application. Examples of monomers include a (meth)acrylamide compound, an N- (or N,N-di)alkyl-substituted (meth)acrylamide derivative, a (meth)acrylamide derivative having a cyclic group, and a vinyl ether derivative. At least one such monomer may be used. When a single type of monomer is used alone, a polymer formed on the substrate is a homopolymer. When a plurality of types of monomers are used, a polymer formed on the substrate is a copolymer. Both types of polymers are within the scope of the present invention. When regulation of T is necessary in accordance with the type of grown cell, improvement in the interaction between a coating material and a cell culture support is necessary, or adjustment of the hydrophilic/hydrophobic balance of a cell support is necessary, for example, monomers other than the above monomers may further be added, and copolymerization may be carried out. Further, a graft or block copolymer of the above-described polymer used in the present invention and another polymer or a mixture of the polymer of the present invention and another polymer may be used. Also, crosslinking may be carried out while maintaining properties inherent to the polymer.

A pH-responsive polymer and an ion-responsive polymer that are suitable for preparation of a cell sheet can be adequately selected.

2. Step of Cell Addition

A step of cell addition involves addition of a cell-containing culture solution to a culture vessel having an inner bottom surface, which is or can be made non-cell-adhesive and comprises a concave-convex pattern provided thereon.

Cells used in the present invention are not particularly limited, provided that such cells are cell adhesive. Examples of such cells include: hepatic cells, which are hepatic parenchymal cells; endothelial cells, such as Kupffer cells, vascular endothelial cells, and corneal endothelial cells; epidermal cells, such as fibroblasts, osteoblasts, osteoclasts, periodontal ligament-derived cells, and epidermal keratinocytes; epithelial cells, such as tracheal epithelial cells, alimentary epithelial cells, cervical epithelial cells, and corneal epithelial cells; muscle cells, such as alveolar epithelial cells, pericytes, smooth muscle cells, and cardiac muscle cells; nephrocytes; pancreatic Langerhans islet cells; nerve cells, such as peripheral nerve cells, and optic nerve cells; cartilage cells; and bone cells. These cells may be primary cells that are directly collected from tissue or organs, or they may be of cells lines established from such primary cells after several passages. Further, such cells may be any of undifferentiated embryonic stem cells, pluripotent stem cells, such as pluripotent mesenchymal stem cells, unipotent stem cells, such as unipotent vascular endothelial progenitor cells, or differentiated cells. Also, a single type of cells may be cultured or two or more types of cells may be cultured together.

These cells are cultured via a conventional technique in advance, the cultured cells are treated with trypsin or the like, the resultants are suspended in a culture solution, and the suspension is accommodated in a culture vessel in that state. Any culture solution can be used without particular limitation, provided that it is a common medium used for cell culture in the art. In accordance with the type of a cell used, for example, basal media described in "*Soshiki Baiyou no Gijutsu*" (Tissue Culture Technique), vol. 3, p. 581, the Japanese Tissue Culture Association (ed.), Asakura Publishing Co., Ltd., such as MEM medium, BME medium, DME medium, αMEM medium, IMDM medium, ES medium, DM-160 medium, Fisher medium, F12 medium, WE medium, and RPMI1640 medium, can be used. Further, serum (e.g., fetal bovine serum), various growth factors, antibiotics, or amino acids may be added to the basal medium. Also, commercially available serum-free medium, such as Gibco serum-free medium (Invitrogen), may be used. When clinical applications of cellular tissue that is obtained at the end are taken into consideration, use of a medium free of animal-derived components is preferable.

3. Step of Cell Culture

The step of cell culture comprises performing cell culture under conditions in which intercellular adhesion takes place while centrifugal or magnetic force toward the inner bottom surface is applied to the cells that were added to the culture vessel and forming tissue via intercellular adhesion. FIG. 1B represents this step. In this step, cells are in close contact with the inner bottom surface with the aid of centrifugal or magnetic force in accordance with the configuration of the inner bottom surface, and cells adhere to each other in such state. Thus, tissue of a desired configuration is formed.

The magnitude of centrifugal force can be adequately selected within a range such that tissue can be formed without adversely affecting cellular functions. For example, centrifugal force is preferably 2 G to 1440 G, and more preferably 2 G to 720 G. By mounting a culture vessel that accommodates a cell-containing culture solution in a centrifuge and performing centrifugation, centrifugal force can be applied.

When magnetic force is allowed to act on cells, it is necessary to magnetize cells with the aid of magnetic fine particles and then perform the aforementioned step of cell addition. The method for magnetizing cells with magnetic fine particles disclosed in Patent Document 1 can be employed. Examples of magnetic fine particles include magnetic fine particles, such as magnetite particles, which had been modified to be held by cells. As disclosed in Patent Document 1, specifically, magnetic fine particles can be used in the form of, for example, a magnetic particle cationic liposome (MPCL) enclosing magnetic fine particles in a liposome or an antibody-immobilized magnetoliposome (AML) enclosing magnetic fine particles in an antibody-immobilized liposome. Further, magnetic microbeads of MACS (the magnetic cell sorting and separation of biomolecules system) (Dai-ichi Kagaku) or magnetic nanoparticles (tradename: EasySep; Veritas) can be used. Such magnetic fine particles are brought into contact with and immobilized on cells, and such particles can magnetize cells.

Magnetic force toward the inner bottom surface can be applied to the cells that were added to the culture vessel by placing a magnet outside the bottom surface of the culture vessel, for example. The magnitude of magnetic force can be adequately determined in accordance with various conditions, such as a cell type, a magnetic fine particle type, and a material of a culture vessel, so that cells inside the culture vessel are gravitated to the inner bottom surface.

In the present invention, it is particularly preferable that culture is conducted by applying centrifugal force to cells. When magnetic force is applied, it is essential to introduce magnetic fine particles into cells. However, inclusion of foreign matter, such as magnetic fine particles, is not preferable when the prepared tissue is used for transplantation into a biological body. When centrifugal force is applied, addition of foreign matter to cells is not necessary, and tissue that is suitable for transplantation can be obtained.

The term "conditions in which intercellular adhesion takes place" refers to conditions in which cells act and cells can adhere to each other. For example, temperature is preferably 20° C. to 40° C., atmospheric gas concentration is preferably 3% to 5% carbon dioxide, and culture duration is preferably 0.5 to 24 hours, although such conditions vary in accordance with the type of a cell to be cultured. An advantage of the present invention is that culture duration can be shortened and a damage imposed on cells can be reduced. Culture duration can be shortened according to an embodiment described below in which an extracellular matrix is separately prepared and added, and culture duration can be shortened to 0.5 to 3 hours. Thus, such embodiment is preferable. According to an embodiment in which an extracellular matrix is not added, culture duration can be 1 to 24 hours.

In the examples, a culture vessel accommodating a cell suspension was allowed to stand for several minutes in an incubator filled with an atmospheric gas of interest (5% carbon dioxide), the culture vessel was covered with a lid so as to maintain the atmospheric gas conditions, and culture was conducted by applying centrifugal force. However, culture is not limited to the above-described methods. For example, culture can be carried out by applying centrifugal force while maintaining the culture vessel in an open state in an incubator in which the atmospheric gas and temperature conditions are regulated.

In the step of cell culture, it is sufficient if intercellular adhesion takes place, and an increase in the number of cells via multiplication is not essential. This is because the thickness of tissue prepared (i.e., the number of cell layers in the through-thickness direction of tissue) can be controlled by adequately regulating the number of cells in a culture solution. Since cell multiplication is not necessary in the step of cell culture, tissue can be obtained within a relatively short period of time. Also, tissue thickness and configuration can be freely regulated. As described above, for example, a cell sheet having through-holes can be formed by regulating the number of cells in the culture solution so as to accumulate cells selectively in concave portions on the inner bottom surface of the culture vessel upon application of centrifugal or magnetic force. As shown in FIG. 13 (Example 2), the number of cells in the culture solution may be regulated so as to cover the top surfaces of concave portions as well as convex portions on the inner bottom surface of the culture vessel with cells upon application of centrifugal or magnetic force. Thus, an inverted pattern of the concave-convex pattern on the inner bottom surface of the culture vessel can be formed on the tissue surface.

According to the method of the present invention, tissue comprising densified cells can be obtained. Such tissue comprising densified cells is preferable for transplantation.

4. Step of Detachment

The step of detachment comprises detachment and collection of tissues obtained after centrifugation or after the release of magnetic force from the inner bottom surface of the culture vessel. For example, cells can be detached via a physical operation such as pipetting. If the inner bottom surface of the culture vessel is non-cell-adhesive, such operation is easy. When the inner bottom surface of the culture vessel is a surface which can be converted into a non-cell-adhesive surface, such as a stimuli-responsive polymer, a detachment operation is carried out in the environment in which a surface can be converted into a non-cell-adhesive surface (e.g., at or below the lower limit of the critical temperature).

Figure 4:
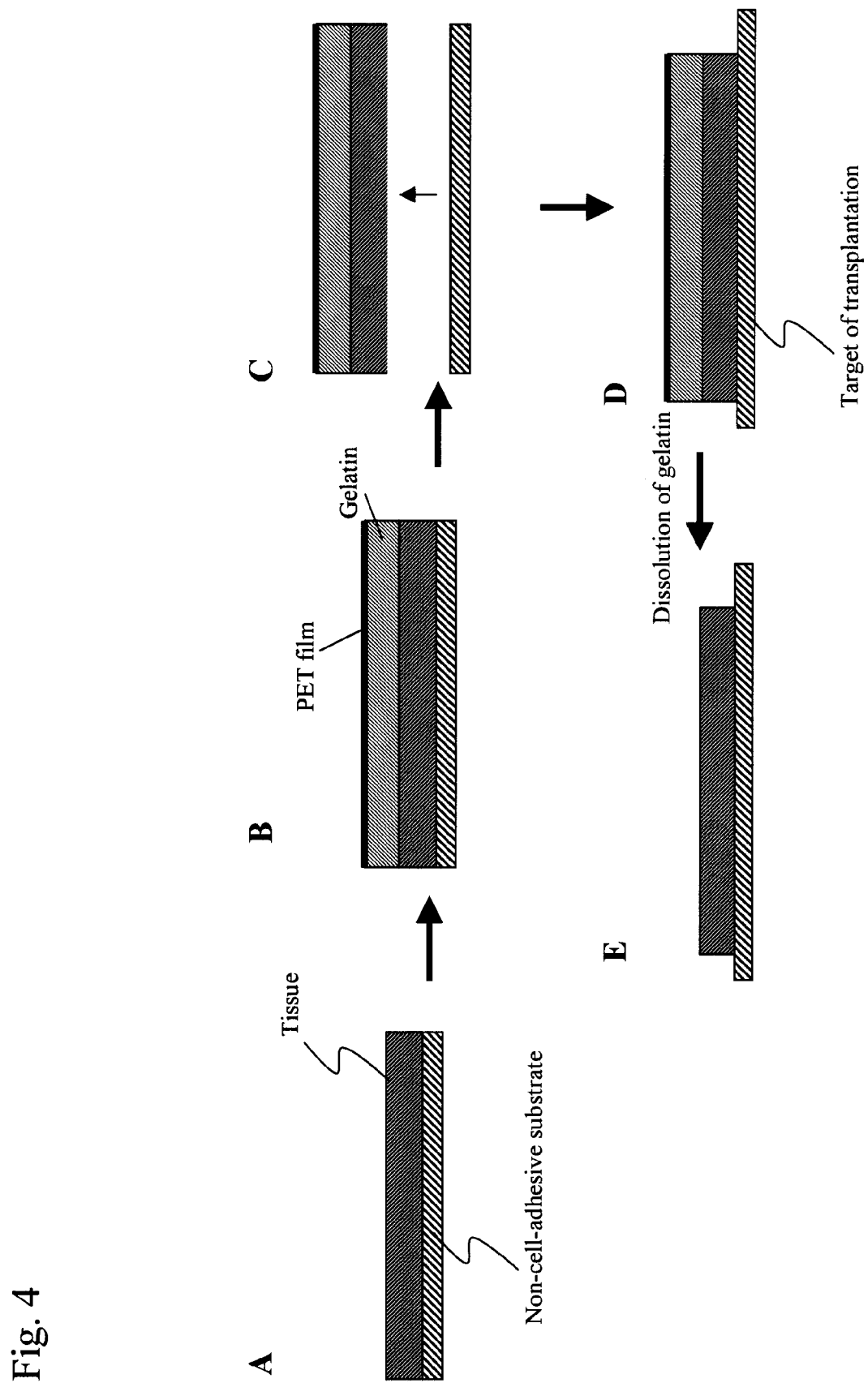
FIG. 4 shows a method for detaching and collecting a cell sheet formed on a non-cell-adhesive substrate.

Detachment may be carried out via a known method as shown in FIG. 4 while maintaining tissue configuration. In FIG. 4, gelatin is first introduced onto the tissue surface formed on a non-cell-adhesive substrate for gelation, gelatin gel is held by a holding substrate, such as a PET film (FIG. 4B), and tissue is then detached and collected from the non-cell-adhesive substrate with gelatin gel (FIG. 4C). The thus-detached and collected tissue is brought into close contact with the target of transplantation (FIG. 4D), gelatin is dissolved at 37° C. (FIG. 4E), and the tissue can then be transplanted to the target of interest.

5. More Preferable Embodiment of the Present Invention

Figure 5:
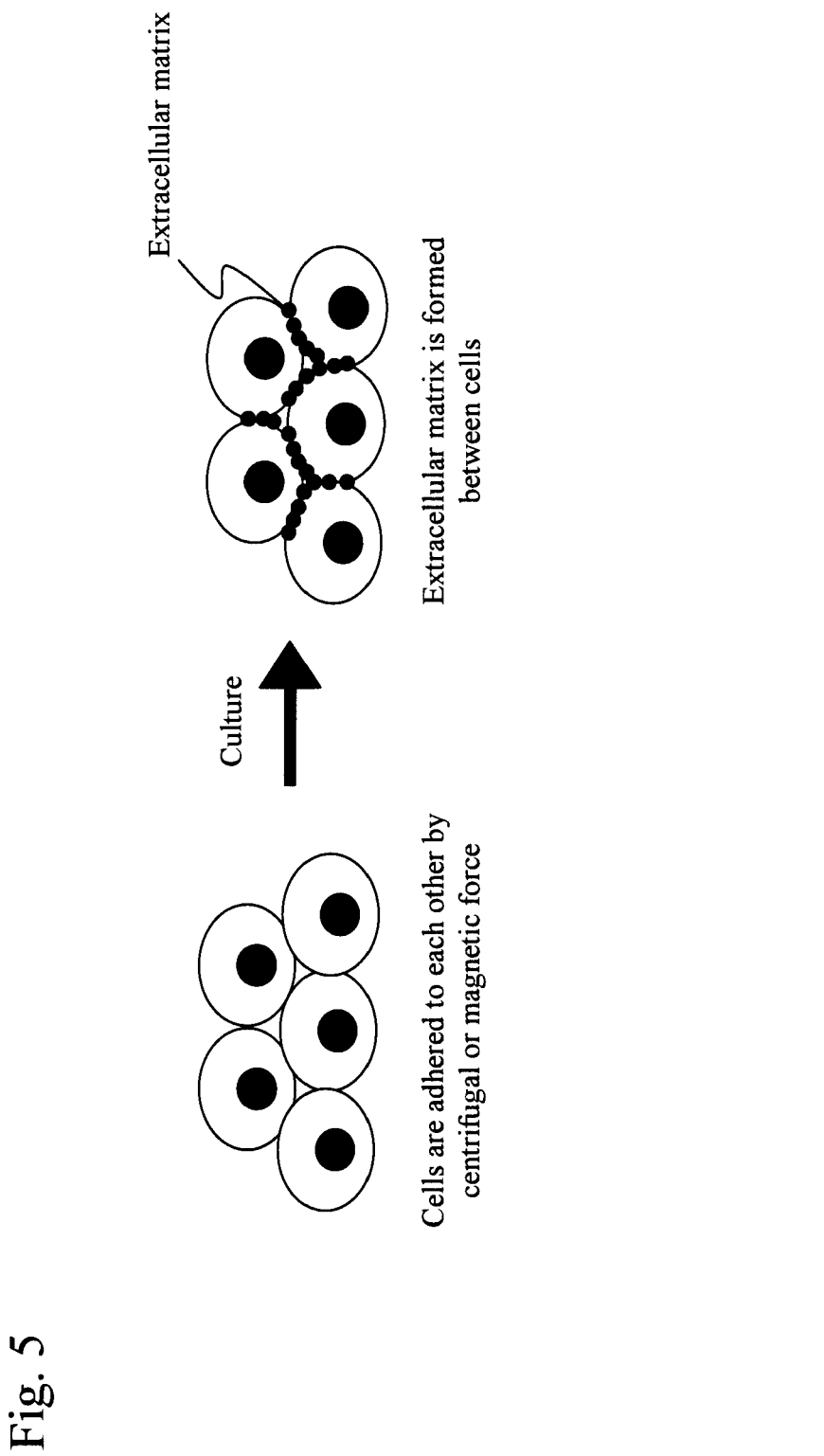
FIG. 5 shows an extracellular matrix.

According to the step of cell culture of the present invention, cells are brought into close contact to each other with the aid of centrifugal or magnetic force, and cells adhere to each other via an extracellular matrix secreted from the cells within several hours (FIG. 5). In general, it takes several hours for the cultured cells to secrete the extracellular matrix.

According to a more preferable embodiment of the present invention, a solution or dispersion of an extracellular matrix component that was separately prepared is added to a culture solution comprising cells suspended therein. Specifically, a culture solution preferably comprises an extracellular matrix component dissolved or dispersed therein. Addition of an extracellular matrix component that was separately prepared can accelerate the speed of intercellular adhesion. According to this embodiment, a step of cell culture can be carried out within 0.5 to 3 hours, tissue preparation can be carried out more efficiently, and the damage imposed on tissue can be minimized.

Figure 6:
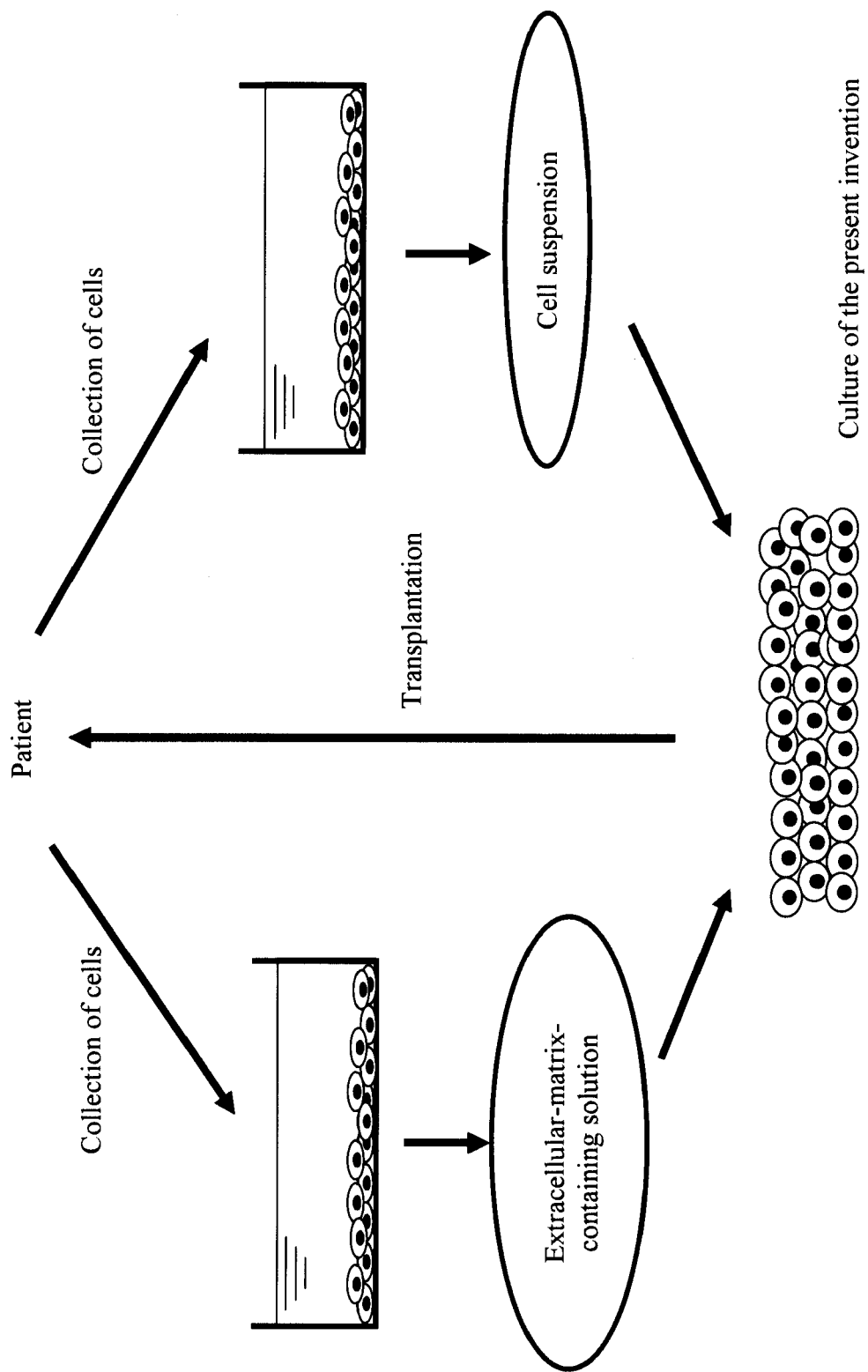
FIG. 6 shows an embodiment of preparation of biological tissue for transplantation involving the use of cells and an extracellular matrix collected from the same patient.

An extracellular matrix is prepared from a cell. A cell used for preparing an extracellular matrix is preferably derived from an individual identical to that from which the cells to be cultured are derived. Since all the biological components of the tissue that is prepared at the end are derived from the same individual, tissue transplantation can be highly safe. FIG. 6 shows a process of preparing tissue by the method of the present invention and transplanting the prepared tissue into a patient. As shown in FIG. 6, it is preferable that cells are collected from a single patient, the collected cells are cultured, a cell suspension is prepared from a culture product, an extracellular matrix-containing solution is prepared from another culture product, both the cell suspension and the solution are used to carry out the aforementioned steps of cell addition, cell culture, and detachment to prepare tissue, and the obtained tissue is then transplanted into the patient.

Cells used for preparing an extracellular matrix are not particularly limited, provided that such cells can form an extracellular matrix. Examples of such cells include adhesive cells, and specific examples include cells selected from the same group as the group exemplified in the present description as specific examples of cells to be cultured. Cells used for preparing an extracellular matrix are not necessary the same as those to be cultured, although cells of the same type are preferable.

An extracellular matrix component is not necessarily used with an extracellular matrix being purified. Tissue comprising many cells adhered thereto with the aid of an extracellular matrix (e.g., a cell sheet formed on a cell-adhesive substrate) is ground, the ground product is fragmented via ultrasound application, solid matter is separated via centrifugation or via other means, according to need, and the resulting extracellular-matrix-containing solution can be used as an extracellular matrix component. The extracellular-matrix-containing solution comprises an extracellular matrix component dissolved or dispersed therein.

Reference Example 1

Figure 7:
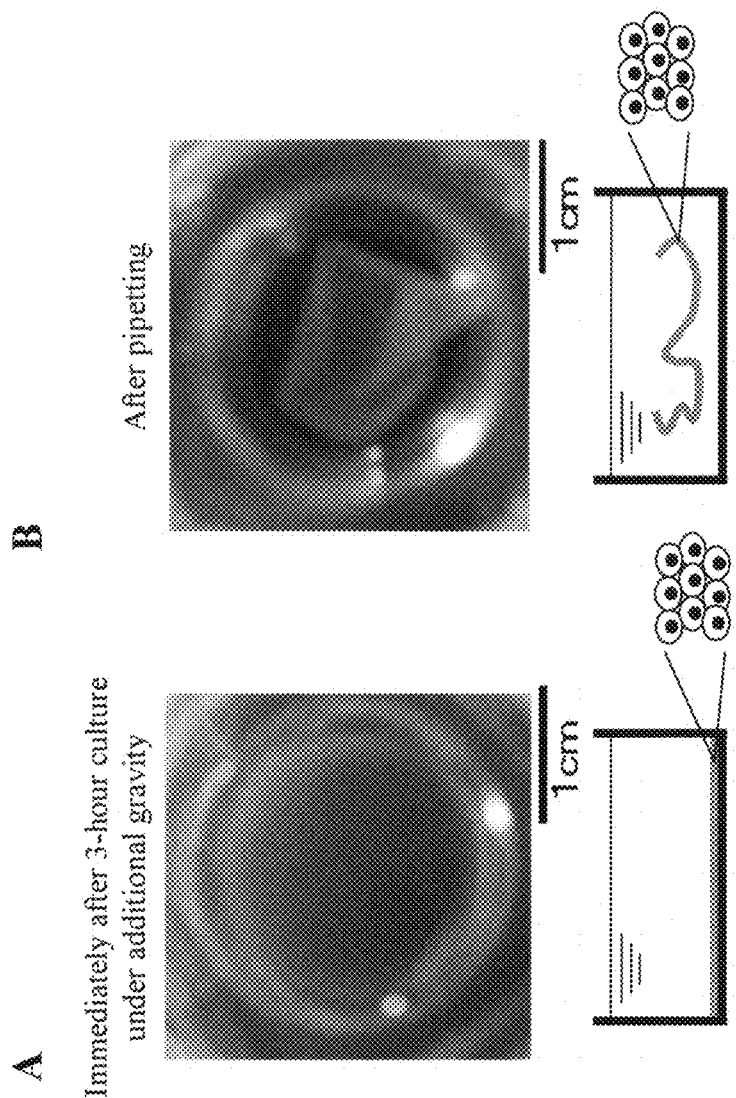
FIG. 7 shows a cell sheet prepared in Reference Example 1.

1. Preparation of Cell Sheet with Centrifugal Force 1-1. Preparation and Collection of Cell Sheet with Centrifugal Force Polyethylene glycol was chemically applied to the entire inner surface of a glass vessel having a bottom with a diameter of 2 cm to render the entire inner surface non-cell-adhesive, 2 ml of a cell suspension containing $4 \times 10^6$ mouse fibroblasts suspended in 10% fetal bovine serum-containing DMEM medium was sowed in the vessel, and culture was conducted at 37° C. in the presence of 5% $CO_2$ for 3 hours while applying centrifugal force of 720 G toward the bottom (FIG. 7A). After culture, centrifugation was terminated, and a cell sheet was easily and rapidly detached and collected from the substrate without destruction of the tissue structure by a physical force, such as via pipetting (FIG. 7B). As a contrast, culture was conducted in the same manner, except that no centrifugal force was applied. As a result, a cell sheet could not be prepared, cells were detached from each other via pipetting, and the tissue structure was destroyed.

1-2. Observation and Live/Dead Assay of Three-Dimensional Tissue

Figure 8:
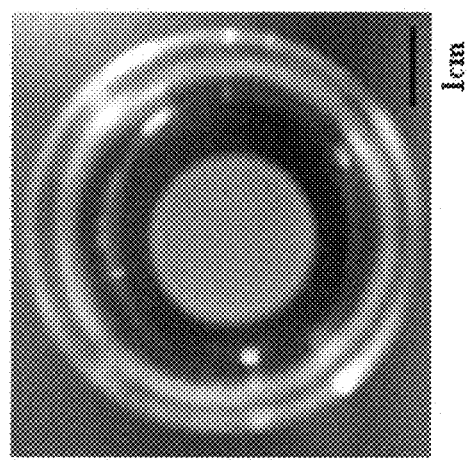
FIG. 8 shows a cell sheet prepared in Reference Example 1.

The cell sheet collected in 1-1 above was transferred to a culture dish for observation and observed. As a result, a cell sheet having a diameter of 2 cm and the same configuration as that of the vessel was obtained (FIG. 8). Also, cells were stained with calcein and subjected to cross-sectional observation under a confocal microscope. As a result, a thickness of the cell sheet was found to be about 3 or 4 cell layers (FIG. 9). In order to inspect the cell survival of the obtained cell sheet, the cell sheet was treated with trypsin and EDTA to disperse cells, and cell viability was assayed using a cell live/dead assay kit (product name: Cell double staining kit; manufacturer: Dojindo Laboratories; product number: CS01). As a result, the cell viability was 90% before application of centrifugal force in 1-1, and the cell viability of the resulting cell sheet was also 90%. The results verify that cells would not be substantially killed by the operation of 1-1.

Reference Example 2

2. Addition of Extracellular Matrix

2-1. Preparation of Extracellular Matrix-Containing Solution

DMEM medium containing 10% fetal bovine serum was added to a 10-cm polystyrene petri dish to culture mouse fibroblasts, and the cells were grown to reach confluence in order to have the cells to produce an extracellular matrix. Subsequently, multiplied cells were ground using a cell scraper, the cells were completely fragmented via ultrasound treatment, the fragmented product was centrifuged, and the supernatant was collected. The supernatant was used below as an extracellular matrix-containing solution.

2-2. Preparation and Collection of Cell Sheet with Centrifugal Force

Figure 10:
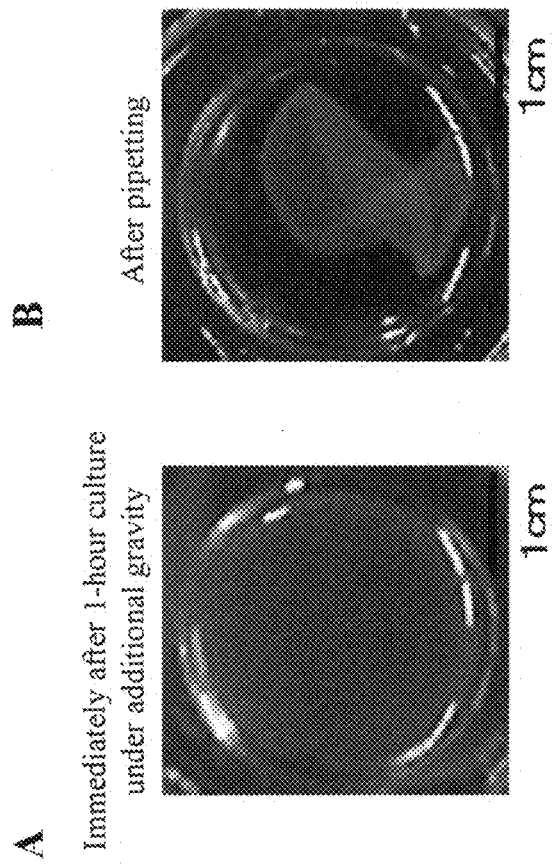
FIG. 10 shows a cell sheet prepared in Reference Example 2.

Polyethylene glycol was chemically applied to the entire inner surface of a glass vessel having a bottom with a diameter of 2 cm to render the entire inner surface non-cell-adhesive, 2 ml of a cell suspension containing $4 \times 10^6$ mouse fibroblasts suspended in the extracellular matrix-containing solution prepared in 2-1 was sowed in the vessel, and culture was conducted at 37° C. in the presence of 5% $CO_2$ for 1 hour while applying centrifugal force of 720 G toward the bottom (FIG. 10A). After culture, centrifugation was terminated, and a cell sheet was easily and rapidly detached and collected from the substrate without destruction of the tissue structure by a physical force, such as via pipetting (FIG. 10B). As a contrast, culture was conducted in the same manner, except that a DMEM medium containing 10% fetal bovine serum was used instead of the extracellular matrix-containing solution prepared in 2-1. As a result, a cell sheet could not be prepared, cells were detached from each other via pipetting, and the tissue structure was destroyed (e.g., the cell sheet was torn).

Example 1

3. Preparation of Cell Sheet Having Holes

Figure 11:
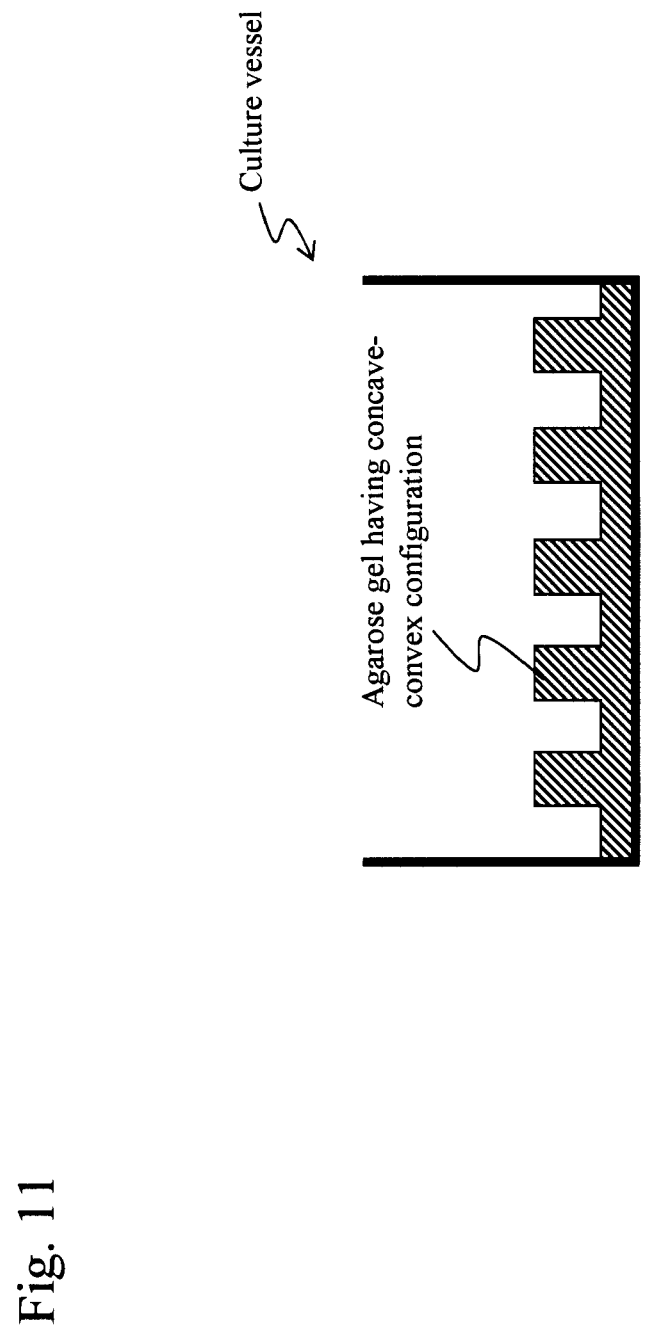
FIG. 11 schematically shows a culture vessel having a concave-convex pattern on the inner bottom surface.

3-1. Culture Vessel Having Non-Cell-Adhesive Bottom Surface with Concave-Convex Configuration A silicon wafer was coated with resist (tradename: SU-8; manufacturer: MicroChem) to a thickness of 200 μm, a concave-convex template was prepared via optical lithography, a 3% agarose solution was introduced onto the template for gelation, and the resulting gel was detached from the template. Thus, agarose gel having a concave-convex pattern (200 μm×200 μm squares raised at heights of 200 μm at intervals of 200 μm) was prepared. FIG. 2 shows the concave-convex pattern of the prepared agarose gel. The resulting gel was positioned at the bottom of the vessel, with the entire inner bottom surface being made non-cell-adhesive in 1-1, so that the concave-convex surface of the gel would face upward. Thus, a culture vessel having a non-cell-adhesive and concave-convex bottom surface was prepared (FIG. 11).

3-2. Preparation of Extracellular Matrix-Containing Solution

DMEM medium containing 10% fetal bovine serum was added to a 10-cm petri dish to culture mouse fibroblasts, and the cells were grown to reach confluence in order to have the cells to produce an extracellular matrix. Subsequently, cells were ground using a cell scraper, the cells were completely fragmented via ultrasound treatment, the fragmented product was centrifuged, and the supernatant was collected. The supernatant was used below as an extracellular matrix-containing solution.

3-3. Preparation and Collection of Cell Sheet with Centrifugal Force

Figure 12:
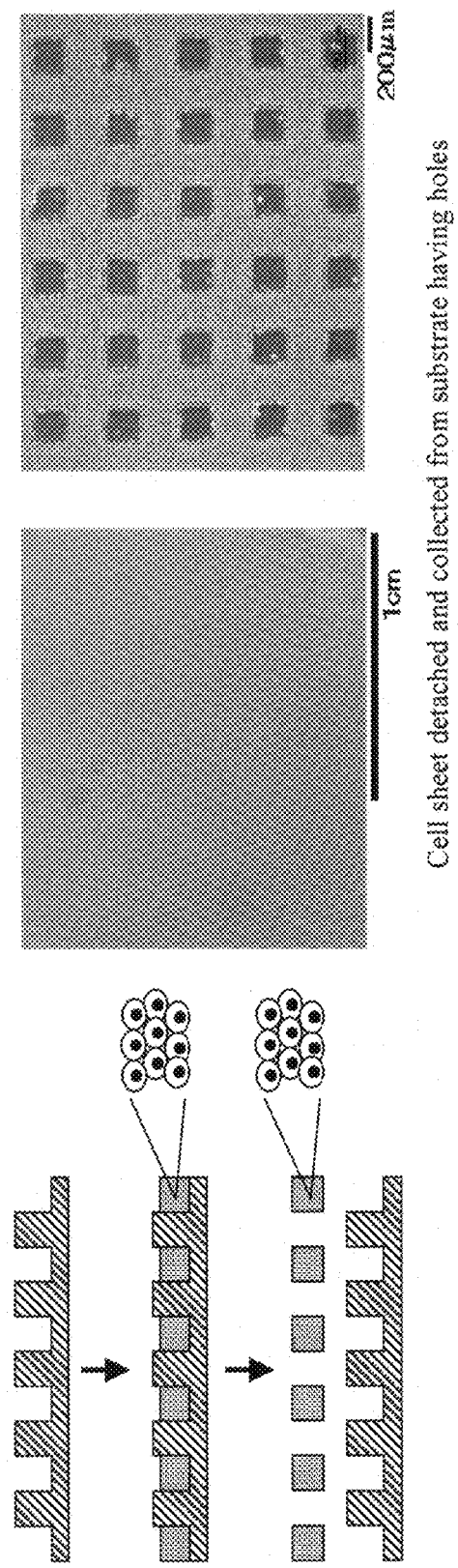
FIG. 12 shows a cell sheet prepared in Example 1 having through-holes.

A cell suspension (2 ml) containing $10 \times 10^6$ mouse fibroblasts suspended in the extracellular matrix-containing solution prepared in 3-2 was sowed in the vessel prepared in 3-1, and culture was conducted at 37° C. in the presence of 5% $CO_2$ for 3 hours while applying centrifugal force of 720 G toward the bottom. Thereafter, centrifugation was terminated, and cell sheets having holes were easily and rapidly detached and collected from the substrate while maintaining the configuration and refraining from destruction of the tissue structure by a physical force, such as via pipetting (FIG. 12).

3-4. Live/Dead Assay of Cell Sheet Having Holes

The cell sheet having 200 μm×200 μm square-shaped holes at intervals of 200 μm prepared in 3-3 was transferred to a polystyrene dish for cell culture, the cell sheet was cultured for 4 days, the cell sheet was treated with trypsin and EDTA to disperse cells, and cell viability was assayed using a cell live/dead assay kit (product name: Cell double staining kit; manufacturer: Dojindo Laboratories; product number: CS01). The cell viability was 86%. Also, a cell sheet without holes was prepared with the use of a culture vessel having the same type of flat bottom surface as that of 3-3, the cell sheet was also cultured for 4 days, and the cell viability was assayed and found to be 70%.

Example 2

Preparation of Cell Sheet Having Patterned Configuration

In the same manner as in 3-1 above, a vessel having a bottom surface (such bottom surface comprising a plurality of parallel lines provided at intervals of 300 µm, raised at heights of 50 µm, and having widths of 200 µm) was prepared using a concave-convex template coated with resist (thickness: 50 µm). The thus-prepared vessel was used to prepare a cell sheet in the same manner as in 3-3, except that cell density was regulated so as to cover the convex ribs as well as lined concave grooves with cells. Thus, a cell sheet having a patterned configuration was prepared (FIG. 13).

The invention claimed is:

1. A method for preparing tissue comprising:
a step of cell addition, wherein said cell is a hepatic cell, hepatic parenchymal cell, endothelial cell, Kupffer cell, vascular endothelial cell, corneal endothelial cell, epidermal cell, fibroblast, osteoblast, osteoclast, periodontal ligament-derived cell, epidermal keratinocyte, epithelial cell, tracheal epithelial cell, alimentary epithelial cell, cervical epithelial cell, corneal epithelial cell, muscle cell, alveolar epithelial cell, pericyte, smooth muscle cell, cardiac muscle cell, nephrocytes, pancreatic Langerhans islet cell, nerve cell, peripheral nerve cell, optic nerve cell, cartilage cell, bone cell, undifferentiated embryonic stem cell, pluripotent stem cell, pluripotent mesenchymal stem cell, unipotent stem cell, unipotent vascular endothelial progenitor cell, or differentiated cell; comprising adding a cell-containing culture solution comprising said cells to a culture vessel having an inner bottom surface, which is or can be converted into a non-cell-adhesive surface and comprises a concave-convex pattern provided thereon;
a step of cell culture comprising performing cell culture under conditions in which at least a part of said cells are accumulated, and intercellular adhesion takes place, at least in the concave portion of said concave-convex pattern upon the application of centrifugal or magnetic force to said cells toward said inner bottom surface, to thereby form tissue via said intercellular adhesion; and
a step of detachment comprising detaching and collecting the tissue obtained in the step of cell culture from the inner bottom surface,
the method further comprising, when magnetic force is applied in the step of cell culture, a step of magnetization comprising magnetizing cells with magnetic fine particles prior to the step of cell addition.

2. The method according to claim 1, wherein the number of cells in the culture solution is regulated in accordance with the number of cell layers in the through-thickness direction of tissue to be prepared.

3. The method according to claim 1, wherein the culture solution contains an extracellular matrix component in a dissolved or dispersed state.

4. The method according to claim 3, wherein the extracellular matrix component is prepared from another cell-containing culture solution comprising cells intrinsically producing the extracellular matrix and derived from an individual identical to that from which the cells to be cultured are derived.

5. The method according to claim 1, wherein a configuration of the concave-convex pattern enables detachment of tissue formed on the inner bottom surface of the culture vessel while maintaining the tissue configuration.

6. The method according to claim 1, wherein the concave-convex pattern comprises a plurality of island-like convex portions and sea-like concave portions continuously formed around the convex portions and the number of cells in a culture solution is regulated, so that the thickness of tissue to be prepared does not exceed the height of the convex portion.

7. The method according to claim 1, wherein the step of cell culture comprises performing cell culture under conditions in which intercellular adhesion takes place while centrifugal force toward the inner bottom surface is applied to the cells that were added to the culture vessel to form tissue via intercellular adhesion.

8. The method according to claim 1, wherein all portions on the inner surface of the culture vessel that are in touch with cells are or can be made non-cell-adhesive.

* * * * *